United States Patent [19]

Rogers

[11] Patent Number: 5,336,223
[45] Date of Patent: Aug. 9, 1994

[54] TELESCOPING SPINAL FIXATOR

[76] Inventor: Charles L. Rogers, 1446 Creekside Ct., Vienna, Va. 22182

[21] Appl. No.: 15,362

[22] Filed: Feb. 4, 1993

[51] Int. Cl.⁵ .............................................. A61F 5/00
[52] U.S. Cl. ......................................... 606/61; 623/17
[58] Field of Search .................... 606/61, 60, 53, 63, 606/72, 105; 623/17

[56] References Cited

U.S. PATENT DOCUMENTS

| | | | |
|---|---|---|---|
| 3,987,499 | 10/1976 | Scharbach et al. | 606/61 |
| 4,401,112 | 8/1983 | Rezaian | 606/61 |
| 4,528,702 | 7/1985 | Frey | 623/23 |
| 5,059,193 | 10/1991 | Kuslich | 606/61 |
| 5,084,048 | 1/1992 | Jacob et al. | 606/61 |
| 5,092,867 | 3/1992 | Harms et al. | 606/61 |
| 5,154,718 | 10/1992 | Cozad et al. | 606/61 |
| 5,171,278 | 12/1992 | Pisharodi | 623/17 |
| 5,246,458 | 9/1993 | Graham | 623/17 |

FOREIGN PATENT DOCUMENTS 3802933  9/1988  Fed. Rep. of Germany ........ 606/61

Primary Examiner—Stephen C Pellegrino
Assistant Examiner—Guy V. Tucker
Attorney, Agent, or Firm—J. W. Gipple

[57] ABSTRACT

The invention is a telescoping spinal fixator having axially aligned upper and lower bearing elements which fit within opposing cavities in vertebrae. The respective bearing elements are maintained at an adjustable distance apart by a connecting rod with a rotatable collar axially mounted intermediate the two bearing elements for adjusting the distance between the bearing elements. In its collapsed configuration, the two bearing elements are aligned proximate to one another with just sufficient space to permit access to the adjustment collar, which is otherwise disposed within cavities in each of the bearing elements.

9 Claims, 2 Drawing Sheets

TELESCOPING SPINAL FIXATOR

SUMMARY OF THE INVENTION

The present invention is directed to a telescoping spinal fixator adapted for placement between respective spinal vertebrae especially to relieve compression on the spinal cord during spinal fusion or other spinal prosthetic procedure. The spinal fixator of the invention is particularly characterized by being expandable once it is inserted in position between respective vertebrae on either side of an excised vertebrae and by having the two ends of the spinal fixator actually disposed within cavities in the vertebrae to prevent lateral movement and disengagement.

BACKGROUND OF THE INVENTION

Various techniques have been used for many years for the surgical treatment of spinal fractures. These technique have included laminectomy and various plate and screw procedures. U.S. Pat. No. 4,401,112 to REZAIAN describes an expandable spinal fixator which is essentially a turnbuckle mounted between upper and lower bearing members, each of which essentially is a pedestal which rests on and engages the opposing surfaces of the vertebrae between which it is placed. Although, the device permits extension of the fixator once it is in place, its inherent lateral instability makes it necessary for the device to be further anchored by brackets which are stapled to the spinal vertebrae. Further, the type of turnbuckle employed in the patented device severely limits the extent of extension which is possible once the device is in place between the vertebrae. Additional extension, once the device is anchored by the supporting plates, then becomes impossible unless these plates are first disengaged from the vertebrae to which they are stapled.

Particularly in view of the dire consequences which attach to any lateral slippage or movement in spinal fixators and the need which often arises for greater expansion and separation between the vertebrae, a purpose of the present invention is to provide an improved spinal fixator which can both be securely anchored between the vertebrae so that lateral movement or slippage is virtually eliminated and which can be extended to a greater extent than has heretofore been possible using devices of the prior art and subsequently removed the following completion and recovery from prosthesis.

DETAILED DESCRIPTION OF THE INVENTION

In accordance with the present invention a spinal fixator is provided which comprises upper and lower bearings elements for engaging respective upper and lower vertebrae within cavities that are formed in each of the vertebrae. An elongated threaded rod connects and extends between the two bearing members. Disposed coaxially intermediate the two bearings with the connecting rod is an adjustment collar which can be rotated to increase or decrease the distance between the two bearing members. A particularly unique feature of the present invention is the extent to which the entire device can be collapsed along its longitudinal axis to provide a compact unit of reduced longitudinal dimensions to facilite insertion between the respective vertebrae. This unique compactness is achieved in part by providing cavities in each of the bearing elements to accommodate a substantial portion of the adjustment collar. The device of the invention is further characterized in that the respective bearing elements are each specifically adapted to be placed within an excavated cavity in one of the opposing vertebrae between which the device of the invention is placed. This feature of the invention is especially significant for avoiding lateral displacement of the fixator and eliminating the need for external supporting brackets.

The invention will however, be more fully appreciated by having specific reference to the drawings which illustrate a preferred embodiment thereof.

Figure 1:
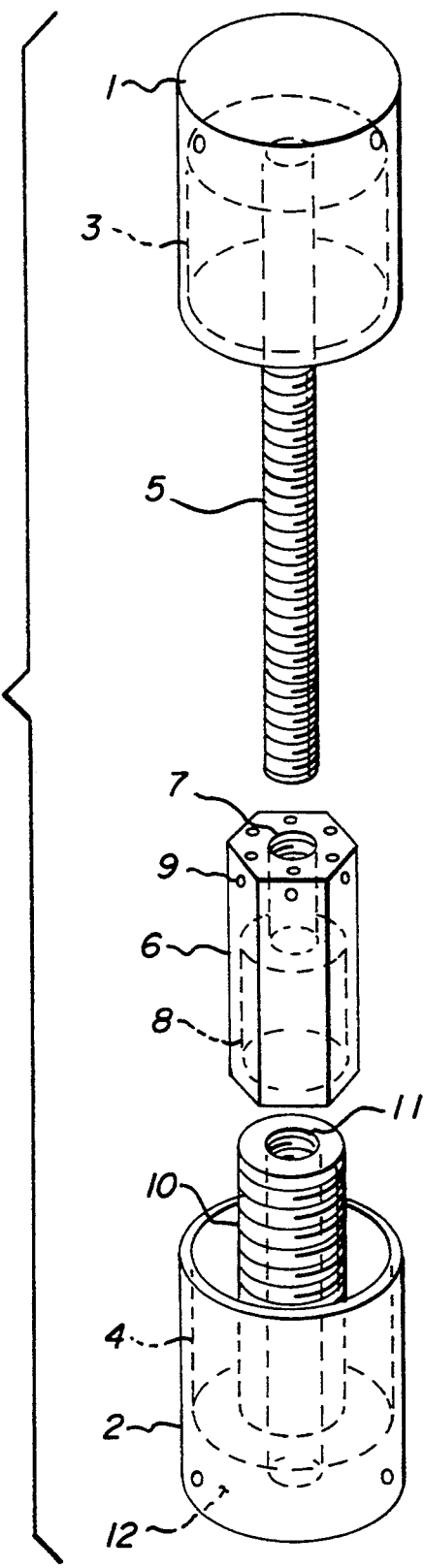
FIG. 1 is an exploded view of the invention illustrating its respective components.

Directing attention initially to FIG. 1 of the drawings, which is an exploded view of the device of the invention illustrating in detail its respective components, upper and lower bearing elements 1 and 2, which are preferably of eliptical or other non-circular cross-section to inhibit rotation within the vertebral cavity, are shown having respective hollow cavities therein, 3 and 4. Anchored to the bearing element 1 and mounted coaxially with it in cavity 4 is elongated threaded rod 5, having (in this instance) a left handed thread. Elongated adjustment collar 6 is illustrated having a hexagonal configuration to facilitate its being turned by a wrench. It will be understood that other configurations can as well be used to achieve a similar elongation. The adjustment collar 6 is provided at its upper portion with a coaxially bore having female threads which mate with the male threads of rod 5. The lower portion of adjustment collar 6 is provided with a cavity 8 of larger lateral dimensions than the bore 7. This lower cavity is also provided with female threads of opposite hand to those of the rod 5 and bore 7.

The lower bearing element 2 has disposed axially within its hollow cavity 4 a threaded tubular member 10 whose lower end engages solid base 12 and which is provided with male threads for its entire length which mate with the female threads provided in the interior cavity 8 of adjustment collar 6. The tubular member 10 has an axial bore 11 which is smooth and of sufficient lateral dimensions to permit passage through it of threaded rod 5. The smooth unthreaded bore 11 extends the entire length of the tubular member 10 and through the solid base 12 of the bearing element 2. Small holes 9 are conventionally provided in the adjustment collar 6 for insertion of locking pins, wire, or screws, to prevent any rotation of the collar once the device is in place. Advantageously, these holes traverse the corners of the collar 6, rather than extending radially to central bore 7. Similar provisions can be made in bearing elements 1 and 2 to facilitate anchoring within the vertebrae.

Figure 2:
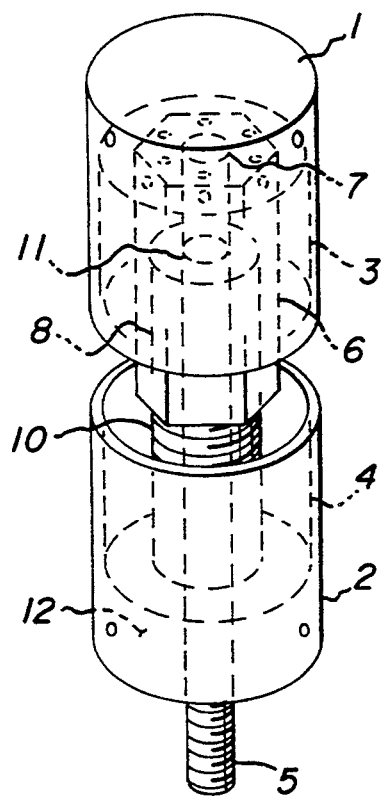
FIG. 2 is perspective view illustrating the device of the present invention in its collapsed configuration prior to insertion between spinal vertebrae.

FIG. 2 illustrates the components shown in exploded view in FIG. 1 in compressed configuration such as is utilized during the insertion procedure contemplated in accordance with the invention. As shown, the upper and lower bearing elements 1 and 2 are aligned to one another with only sufficient space between the two elements for insertion of a wrench to permit turning of the adjustment collar 6. The threaded connecting rod 5 is joined at its upper end to the base of bearing element 1 and at its other end actually extends through the bore 11 to emerge past the bottom of solid base 12 of bearing element 2. Adjustment collar 6 is almost totally contained within the respective cavities 3 and 4 of the bearing elements except for the small portion which is exposed between the respective bearing elements to permit engagement with a wrench or other device for tuning the adjustment collar. Tubular member 10 which is mounted within the cavity 4 of bearing element 2 is otherwise disposed within the cavity 8 of adjustment collar 6 which has female threads which engage the male threads of the tubular member.

It will be appreciated that in order to permit axial displacement of the respective bearing elements 1 and 2 by turning the adjustment collar 6 it is necessary that the threads on rod 5 and their associated threaded mating surfaces be of one hand while the threads of the tubular member 10 and its associated threaded mating surfaces of the other hand. It should also be appreciated that the threads of the rod 5 be of greater pitch then those of the elongated member 10, preferably two to three times the pitch thereof.

Figure 4:
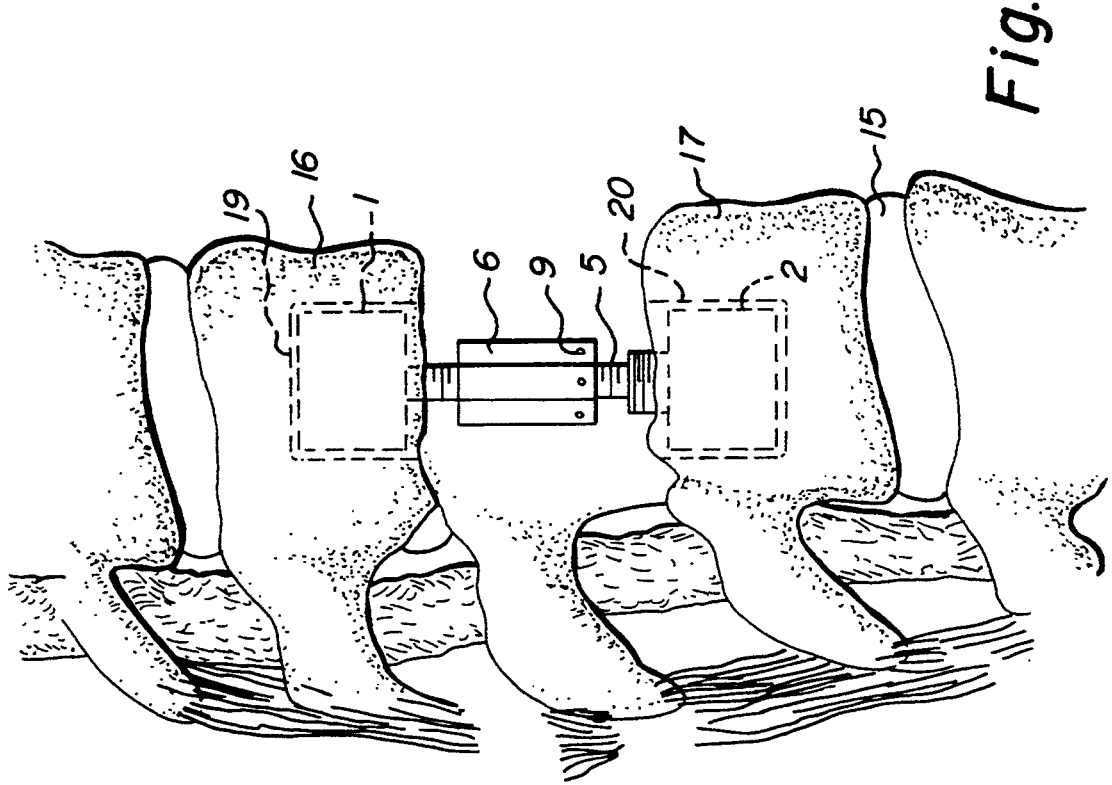
FIG. 4 is a perspective view of a broken spine illustrating the fixator of the invention in place between two vertebrae.
Figure 3:
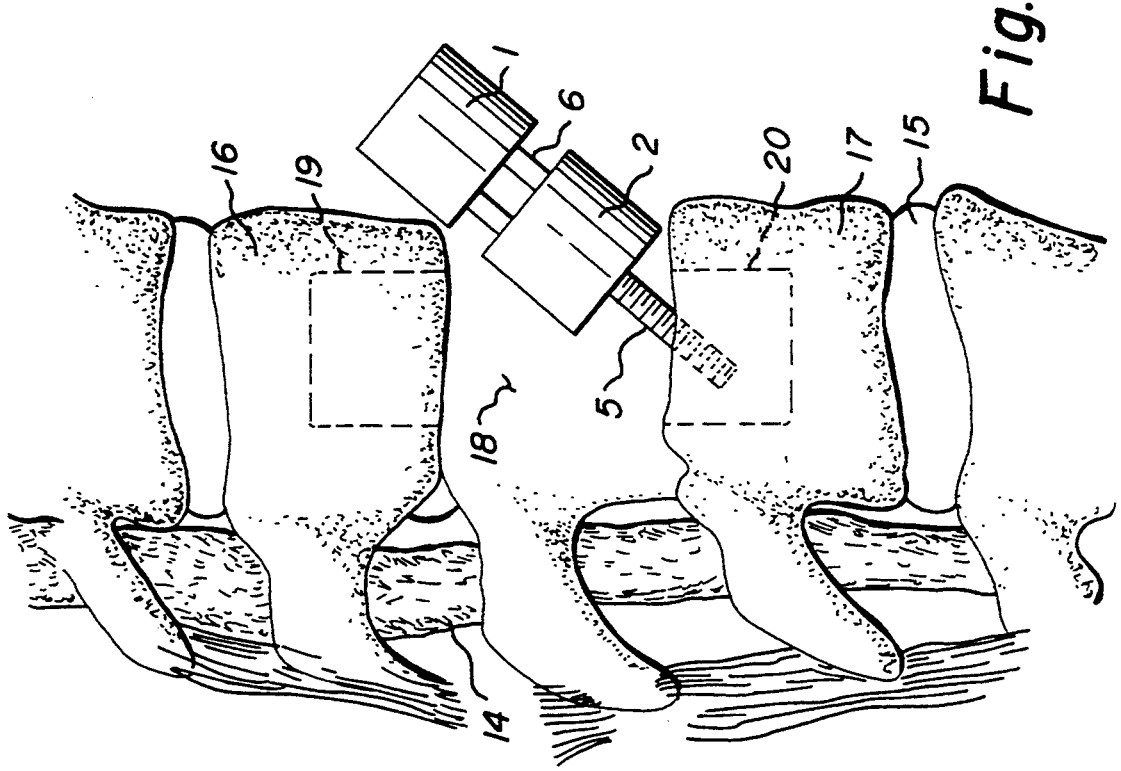
FIG. 3 is a perspective view of a broken spine illustrating the initial procedure for insertion of the fixator between vertebrae.

Insertion of the device of the invention between two spinal vertebrae is illustrated in FIG. 3 of the drawings. As is commonly necessary for prosthetic implants of spinal fixators, a portion of one vertebrae disposed between vertebrae 16 and 17 of the drawings has been removed. By appropriate surgical procedure, cavities 19 and 20 have been provided opposing one another in the respective vertebrae 16 and 17. In order to achieve decompression of the spinal cord 14, the device of the invention is implanted in cavities 19 and 20 in respective vertebrae 16 and 17 adjacent excised vertebrae 18. The lower protruding end of the threaded connecting rod 5 is initially disposed within cavity 20 while the device of the invention is in its compressed or telescoped configuration as illustrated in FIG. 2 of the drawings. Upper bearing element 1 is then inserted within cavity 19 so that it rests securely within the cavity. In order to further prevent movement within the cavity appropriate surgical cement such as methyl methacrylate or fixation devices maybe employed. With the device properly aligned vertically between the respective vertebrae and with the upper bearing 1 firmly engaged within cavity 19, adjustment collar 6 is rotated in the appropriate direction to cause expansion of the device of the invention. This expansion takes place by linear displacement of bearing element 2 relative to the upper bearing 1 so that eventually the device is disposed as illustrated in FIG. 4 of the drawings. As seen in FIG. 4 of the drawings the lower bearing element 2 is firmly seated within cavity 20 in vertebrae 17 in the same manner as the upper bearing element 1 is seated in cavity 19. Adjustment collar 6 is now fully exposed and located outside of the interior portions of the respective bearing elements. As previously noted, once the device is properly implanted between the vertebrae and the desired extension has been achieved, it is desirable to place locking pins or other devices in the adjustment collar to prevent accidental rotation and compression of the device. It will be appreciated by those of ordinary skill in the art that the device of the invention can be constructed of various materials having the strength, durability and physiological acceptability required for such prosthetic implants. Typical materials can be, for examples stainless steel and titanium which may be provided with a roughened to porous surface to facilitate adhesion to the bone.

Various modifications and equivalent variations in the invention will also be apparent and are considered to fall within the scope of the invention.

What is claimed:

1. A telescoping spinal fixator comprising first and second bearing means for engaging respective spinal vertebrae within cavities formed therein and maintaining said engaged vertebrae in an extended relationship from one another; said first and second bearing means being connected together along an axis at an adjustable distance by telescoping connecting, rods axially disposed between them and a rotatable distance adjusting means mounted coaxially on each of said rods intermediate said respective bearing means; each of said bearing means having an open, hollow interior cavity for accommodating at least a portion of one of said rods and said adjusting means when said bearing means are adjusted to be proximate to one another.

2. The spinal fixator of claim 1 wherein said adjusting means is a sleeve coaxially mounted on said rods and having interior, threads to engage threads on said rods.

3. The spinal fixator of claim 2 wherein one of said rods is a tubular member disposed within the cavity of one of said bearing means coaxially to the other of said rods and having a smooth bore adapted to accommodate passage of said other rod.

4. The spinal fixator of claim 3 wherein said tubular member has threads of opposite hand to the threads of said other rod, and said adjusting means has an interior cavity with threads to mate with those of said tubular member.

5. The spinal fixator of claim 4 wherein the pitch of the treads of said other rod is greater than the pitch of the threads of said tubular member.

6. The spinal fixator of claim 3 wherein said other rod projects axially through said tubular member when said first and second bearing means are adjusted proximate to one another.

7. The spinal fixator of claim 1 wherein said distance adjusting means is provided with means for preventing rotation thereof.

8. The spinal fixator of claim 1 wherein said bearing means are non-circular in cross section.

9. A spinal fixator comprising first and second bearing means each having an open hollow interior cavity for engaging within respective vertebrae above and below a broken or diseased vertebrae portion; said bearing means being adapted to fit within said respective vertebrae; the interior of one of said bearing means engaging one end of a coaxial, treaded elongated rod whose other end engages the interior of a cooperating treaded proximal portion of an elongated tubular adjusting means having a hollow bore; a distal portion of said adjusting means having a greater interior diameter than said proximal portion and having threads of the opposite hand from the proximal threads; the other of said bearing means having a hollow, tubular shaft disposed coaxially therein having threads and dimensions to engage with the threaded distal portion of said adjusting means and having a smooth bore of sufficient size to accommodate passage of said elongated rod; the hollow interior cavities of said bearing means being of sufficient size to accommodate at least a portion of one of said rods and said adjusting means when said bearing means are adjusted to be proximate to one another.

* * * * *